United States Patent [19]

Jordan

[11] 4,133,868

[45] Jan. 9, 1979

[54] ISOCYANATES PROCESS III

[75] Inventor: Robert K. Jordan, Pittsburgh, Pa.

[73] Assignee: Idram Engineering Company Est., Vaduz, Liechtenstein

[21] Appl. No.: 825,057

[22] Filed: Aug. 16, 1977

[51] Int. Cl.² .................. C01C 3/14; C07C 118/00
[52] U.S. Cl. ......................... 423/365; 423/483; 260/429 R; 260/544 F; 260/453 P; 562/605; 562/607; 562/480
[58] Field of Search .............. 423/483, 364, 365; 260/453 P, 453 PC, 544 F, 541, 429 R

[56] References Cited

U.S. PATENT DOCUMENTS

| | | | |
|---|---|---|---|
| 3,707,495 | 12/1972 | Mackay et al. | 260/453 P |
| 3,919,278 | 11/1975 | Rosenthal et al. | 260/453 P |
| 3,991,108 | 11/1976 | Jordan | 423/483 X |

*Primary Examiner*—Earl C. Thomas
*Attorney, Agent, or Firm*—Stevens, Davis, Miller & Mosher

[57] ABSTRACT

A process for producing isocyanates along with hydrogen fluoride and metal carboxylates by reacting a metal salt of an N-organic carbamic acid, $RNHCO_2M$, and an acyl fluoride.

4 Claims, No Drawings

ISOCYANATES PROCESS III

This invention relates to a process for the production of isocyanates from metal salts of N-organic carbamates and and acid fluorides of carboxylic acids.

Isocyanates are produced by the phosgenation of the corresponding amines. Thus methyl isocyanate, used in the production of the well known insecticide alpha-naphthyl ester of N-methyl carbamic acid, is made by reacting expensive and hazardous phosgene with methyl amine, or its hydrochloride, which further results in the generation of hydrogen chloride, a relatively useless by-product.

$$CH_3NH_2 + COCl_2 \rightarrow CH_3NCO + 2 HCl$$

Likewise hexamethylenediisocyanate, toluene diisocyanates, methylene bis(4-phenyl isocyanate) and polymethylenepolyphenyleneisocyanates, mostly used in polyurethane elastomers, flexible polyurethane foams and rigid polyurethane foams, are all produced by essentially the same process.

Phosgene itself is expensive and energy intensive, produced from carbon monoxide, of 8.7 million Btu's per ton, and chlorine, of about 15 million Btu's per ton based on approximately half the 3000 Kwh's required per ton of caustic soda and a ton of chlorine. Further, in the production of the important isocyanates for polyurethanes some 1 ton of hydrogen chloride is made as by-product and must be disposed of uneconomically or electrolyzed at the expense of much energy back to chlorine.

Therefore, it is an object of my invention to provide a new and improved process for the production of isocyanates.

My invention is a process for the production of isocyanates comprising combining a metal salt of an N-organic carbamic acid and an acyl fluoride.

I have discovered that by combining an acyl fluoride, for example trifluoroacetyl fluoride, with a metal N-organic carbamate, for example sodium N-methyl carbamate, about in approximately equimolar quantities, methyl isocyanate is produced. Evidently the process proceeds by the generalized equation, $$R'COF + RNHCO_2M \rightarrow R'CO_2M + RNCO + HF$$

and thus valuable metal salts of carboxylic acids and valuable hydrogen fluoride are coproduced by the process. As metal salts of N-monoorganic carbamic acids are easily produced by the process of my U.S. Pat. No. 4,034,037, by the addition of carbon dioxide to solutions containing the corresponding amine and a metal salt of an acid, for example methyl amine and sodium chloride in liquid ammonia, no carbon monoxide is needed. Further, as acyl fluorides are easily produced from metal fluorides, sulfur oxides and either of carboxylic anhydrides or metal carboxylates as described in my U.S. Pat. No. 3,991,108, the use of expensive and energy intensive chlorine is obviated. More, if desired the metal carboxylates produced in the instant invention can be utilized in the production of the acyl fluoride by the process of U.S. Pat. No. 3,991,108.

Clearly in operating the process the presence of the generated hydrogen fluoride can also react with the metal salts of the carbamates, i.e., $$RNHCO_2M + HF \rightarrow RNH_2 + CO_2 + MX$$

it is desirable to employ an excess of the acyl fluoride, or to combine the intermediates in such a way as to insure immediate contact or utilize a solvent or diluent, especially for the metal carbamate, or use a two step heating program. However, it should be noted that some ureas formed by the reaction of the isocyanate with the amine or ammonium carbamate can be partly made into isocyanate with acyl fluorides too, but at great expense. Thus a number of advantageous methods of conducting the process are available. Adding the powders or crystals to a gaseous acyl fluoride as in a fluidized bed or simply to fall through it or to be carried by the gas is useful in that it can be tied directly into the acyl fluoride process. U.S. Pat. No. 3,991,108 shows sulfur trioxide adducts, i.e, calcium fluoride fluorosulfonate and calcium fluorosulfonate, with a metal carboxylate such as sodium acetate are intimately mixed and heated to about 150° C whence acetyl fluoride is evolved in high yield and purity. As the gaseous acyl fluoride is already heated the powdered metal carbamate can be added as it leaves the reactor into a fluid bed, or the powder can fall through the gaseous acyl fluoride, or it can be carried along with the gas through a tube. However done as indicated, the products are easily separated, and a continuous process is the result. The metal carboxylate product being a solid can be separated using a cyclone, a bag filter or by other means well known for separating particulate matter from a gas. The product isocyanate always boils at a different temperature if the reactants are properly selected acyl fluorides are used and typically at a higher temperature than either the acyl fluoride or hydrogen fluoride produced. Only acetyl fluoride and hydrogen fluoride boil closely, 20.8° C and 19.5° C respectively, and even these can be separated rather easily, for example in a column using methyl formate as an entrainer, b.p. 32° C. And there are other ways for their separation such as permeable membranes, solubility differences and even if desired by reacting the acyl fluoride, for example in the Friedel-Crafts process with benzene to produce acetophenone, an intermediate for styrene.

Another method for effecting the reaction of the metal carbamate continuously is by adding the solid powder to the bottom of a tower filled or partly filled with liquid acyl fluoride, ideally such acyl fluoride having a higher boiling temperature than hydrogen fluoride. Ideally then the flow of the acyl fluoride would be such from the bottom, or near the bottom, to carry the particulate matter, both metal carbamate upwards, such that at an upward level the liquid solid mixture would be withdrawn, and the acyl fluoride and isocyanate separated, for example by continuous distilation.

Still another method which has many advantages would utilize a liquid media or solvent for the process in which the metal carbamate would be suspended or dissolved and injected into the above. This would enable using a gaseous acyl fluoride, but using a gaseous acyl fluoride necessitate much mixing to obtain the ideal excess of it to the metal carbamate. More ideal is the use of an acyl fluoride which is a liquid under the conditions intensively mixed with a suspension or solution of the metal carbamate which enables the process to be conducted more closely to the ideal equimolar or equiequalivant. A solvent may also be used for the acyl fluoride.

The ideal liquid media is a solvent for metal carbamate. Ethers are good, especially crown ethers or ethers which behave like crown ethers such as octaethyleneglycol dimethyl ether. These are especially desirable in that they enable hydrocarbons to also be used. But hydrocarbons themselves must be selected judiciously because of the tendency of the acyl fluorides to react with them in a Friedel-Crafts reaction, for example with aromatics. Chlorinated and fluorinated hydrocarbons may be employed, for example dichlorodifluoromethane, although higher molecular weight media of this ilk are preferred. Any media which is relatively inert to the intermediates or products of the process may be employed.

At the least expensive of the acyl fluorides are those having low boiling temperatures, it is ideal to conduct the process under pressure in most methods employing a large excess of the acyl fluoride, up to some 30 atmospheres. When a high boiling solvent or media is employed with a higher boiling acyl fluoride using intensive mixing, the process is best conducted at somewhat above atmospheric pressure, although even reduced pressure may be used. For example if methyl isocyanate is being produce using a high boiling acyl fluoride, for example terephthaloyl fluoride, and the metal carbamate is added as a solid or in a high boiling solvent or media, greatly reduced pressure could be employed. Clearly it is ideal to remove the isocyanate as a gas if possible for several reasons. First many metal salts, especially metal carboxylates and metal carbamates cause isocyanates to polymerize. Second it simplifies the process requiring fewer pieces of apparatus. It should be noted that acyl fluorides and hydrogen fluoride are inhibitors to polymerization by isocyanates.

The process may also be advantageously conducted in two heating stages whence mixing is conducted at a low temperature, and then the mass is rapidly heated. Thus the temperature range of the process is very great, for example from very low temperatures, even −20° C for example, or lower, and up to very high temperatures, for example 400° C. The ideal temperature range is from about 50° C to about 250° C, of course depending on the isocyanate.

The preferred metal salts of carbamates are clearly those of mono-, bi- and tri-valent metal salts of carbamic acids based on methyl amine, hexamethylenediamine, mixtures of 2,4- and 2,6-toluenediamines, 4,4'-diaminodiphenymethane, and others whose isocyanates are employed commercially. Of potential commercial interest too are the isocyanates that can be produced from metal N-butyl carbamate and m-xylyldicarbamate. While the simple acyl fluorides such as formyl, acetyl fluorides are preferred, the other acyl fluorides including the carbonyl fluorides of the whole aliphatic and aromatic series of mono- and poly-fluorides. The nature of the metal carbamate employed insofar as the cation is concerned should be based on known considerations, for example the catalytic activity of the cation to isocyanate polymerization, but tempered with the fact that at higher temperatures that problem is often eliminated. The metal carbamates of U.S. Pat. No. 4,034,037 may be used, ideally the sodium and polyvalent metals having the least effect on isocyanate polymerization and economically reasonable. The range of acyl fluorides useful in the process included those noted in U.S. Pat. No. 3,991,108. And while not nearly as important as isocyanates, isocyanic acid, HNCO, made be produced by the process by utilizing metal salts of carbamic acid instead of N-monoorganic carbamic acid. Otherwise the process is nearly the same with the exception that isocyanic acid is distinctive in posessing a much lower temperature than isocyanates, and in at times possessing a distinctly different structure.

Because the present phosgenation processes for amines and amine hydrochlorides to produce isocyanates necessitates a large excess of phosgene to amino groups, apparatus for that process may be altered and adapted to the instant process, particularly when the lower acyl fluorides are employed. As a solvent is employed in the conventional isocyanate processes, accommodation for handling the metal carboxylate products presents little problem.

According to the provision of the patent statutes, I have explained the principle of my invention and have illustrated and described what I now consider to represent its best embodiment. However, I desire to have it understood that within the scope of the appended claims the invention may be practiced otherwise.

I claim:
1. A process for the production of organic isocyanates comprising combining a metal salt of an N-organic carbamic acid and an acyl fluoride.

2. A process for the production of isocyanic acid comprising combining a metal salt of carbamic acid and an acyl fluoride.

3. A process for the production of organic isocyanates comprising,
   a. adding sulfur trioxide to a metal fluoride to provide a metal fluoride-sulfur trioxide adduct,
   b. combining a metal carboxylate or carboxylic anhydride and said metal fluoride-sulfur trioxide adduct to produce an acyl fluoride, and,
   c. combining the acyl fluoride and a metal salt of an N-organic carbamic acid to produce hydrogen fluoride, a metal carboxylate and an organic isocyanate.

4. A process for the production of isocyanic acid comprising,
   a. adding sulfur trioxide to a metal fluoride to provide a metal fluoride-sulfur trioxide adduct,
   b. combining a metal carboxylate or carboxylic anhydride with said metal fluoride-sulfur trioxide adduct to produce an acyl fluoride, and,
   c. combining the acyl fluoride and a metal salt of carbamic acid to produce isocyanic acid, a metal carboxylate and hydrogen fluoride.

* * * * *

UNITED STATES PATENT AND TRADEMARK OFFICE
CERTIFICATE OF CORRECTION

PATENT NO. : 4,133,868
DATED : January 9, 1979
INVENTOR(S) : Robert K. Jordan

It is certified that error appears in the above-identified patent and that said Letters Patent are hereby corrected as shown below:

On the title page Item [75], should read:
-- Robert K. Jordan
   Carlton House, Suite 1431,
   550 Grant Street
   Pittsburgh, PA 15219 --.

Item [73], delete "Idram Engineering Company
   Est., Vaduz, Liechtenstein".

Same title page delete "Attorney, Agent, or Firm -
   Stevens, Davis, Miller & Mosher".

Signed and Sealed this

Seventeenth Day of July 1979

[SEAL]

Attest:

LUTRELLE F. PARKER

Attesting Officer

Acting Commissioner of Patents and Trademarks